(12) United States Patent
Furuta et al.

(10) Patent No.: US 10,695,021 B2
(45) Date of Patent: Jun. 30, 2020

(54) IMAGE PICKUP APPARATUS FOR BREAST EXAMINATION

(71) Applicant: Shimadzu Corporation, Kyoto-shi (JP)

(72) Inventors: Masafumi Furuta, Kyoto (JP); Kazushige Tachibana, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 88 days.

(21) Appl. No.: 15/128,463

(22) PCT Filed: Dec. 11, 2014

(86) PCT No.: PCT/JP2014/082890
§ 371 (c)(1),
(2) Date: Sep. 23, 2016

(87) PCT Pub. No.: WO2015/145889
PCT Pub. Date: Oct. 1, 2015

(65) Prior Publication Data
US 2017/0105693 A1    Apr. 20, 2017

(30) Foreign Application Priority Data
Mar. 26, 2014 (JP) .................................. 2014-063593

(51) Int. Cl.
*A61B 6/00* (2006.01)
*A61B 6/04* (2006.01)
(Continued)

(52) U.S. Cl.
CPC ............ *A61B 6/502* (2013.01); *A61B 6/0435* (2013.01); *A61B 6/107* (2013.01); *A61B 6/4208* (2013.01);
(Continued)

(58) Field of Classification Search
CPC ...... A61B 6/502; A61B 6/0435; A61B 6/4208
See application file for complete search history.

(56) References Cited

FOREIGN PATENT DOCUMENTS

| JP | 2008-99930 A | 5/2008 |
|---|---|---|
| JP | 2012-10772 A | 1/2012 |

(Continued)

OTHER PUBLICATIONS

English translation of JP 2013-022041 (Year: 2013).*
(Continued)

*Primary Examiner* — Eric D. Bertram
(74) *Attorney, Agent, or Firm* — Muir Patent Law, PLLC

(57) ABSTRACT

An image pickup apparatus for breast examination capable of reliably imaging an entire breast is provided. That is, according to this invention, a breast introduced into a detector ring can be placed reliably in a radiographic field of view of the apparatus. That is, the image pickup apparatus for breast examination according to this invention includes a support at an opening opposite to an opening at a side, where a breast of a patient is inserted, of a through-hole of the detector ring. A tip of the breast introduced into the detector ring is obstructed by this support, and cannot project outside the detector ring but contacts a contact surface located in the radiographic field of view. According to this invention, the tip of the breast does not project outside the radiographic field of view, and the breast introduced in the detector ring can be positioned reliably in the radiographic field of view of the apparatus.

12 Claims, 6 Drawing Sheets

(51) Int. Cl.
  *A61B 6/10* (2006.01)
  *A61B 6/03* (2006.01)
(52) U.S. Cl.
  CPC ............ *A61B 6/4258* (2013.01); *A61B 6/481* (2013.01); *A61B 6/583* (2013.01); *A61B 6/037* (2013.01)

(56) References Cited

FOREIGN PATENT DOCUMENTS

| JP | 2013-022040 | * | 2/2013 | ............... A61B 6/03 |
| JP | 2013-22040 A | | 2/2013 | |

OTHER PUBLICATIONS

Drawings of JP 2013-022041 (Year: 2013).*
International Search Report of PCT/JP2014/082890, dated Feb. 24, 2015.

* cited by examiner

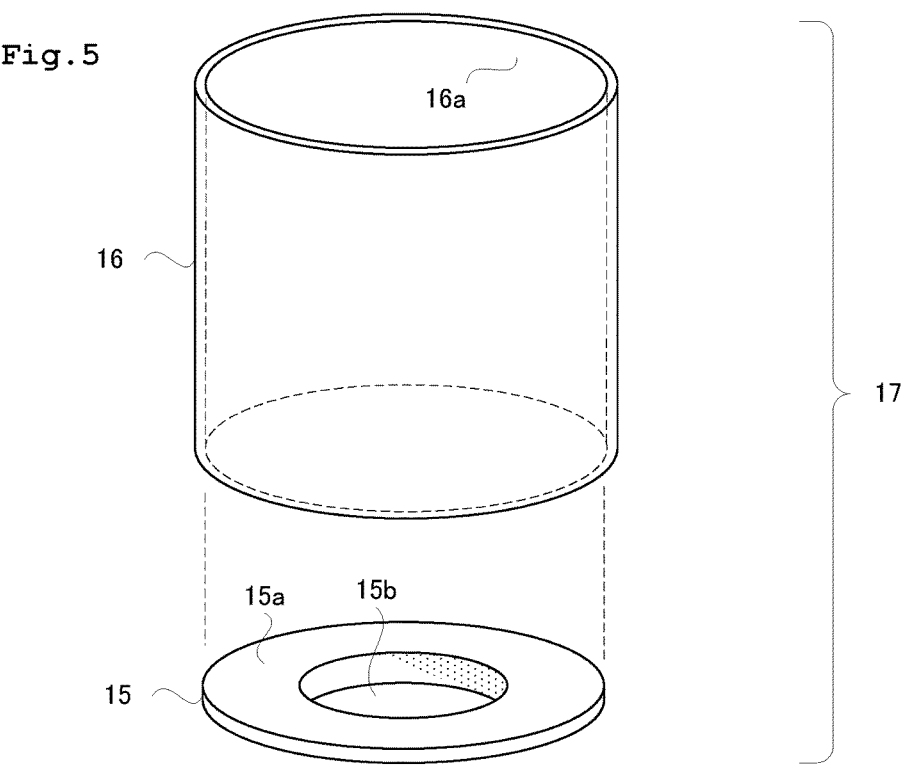
Fig.5
Fig.6
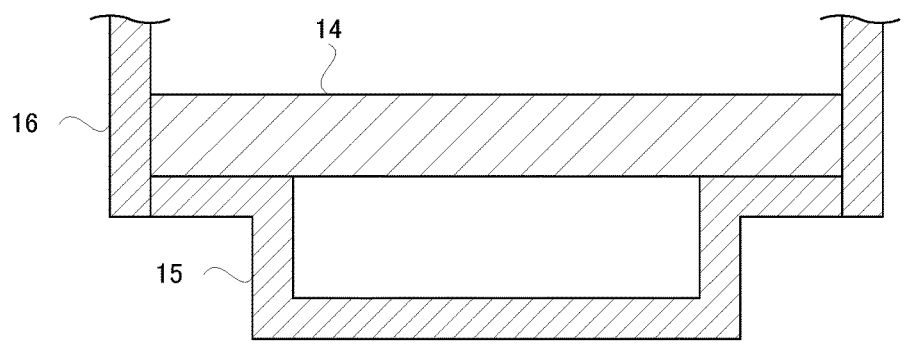
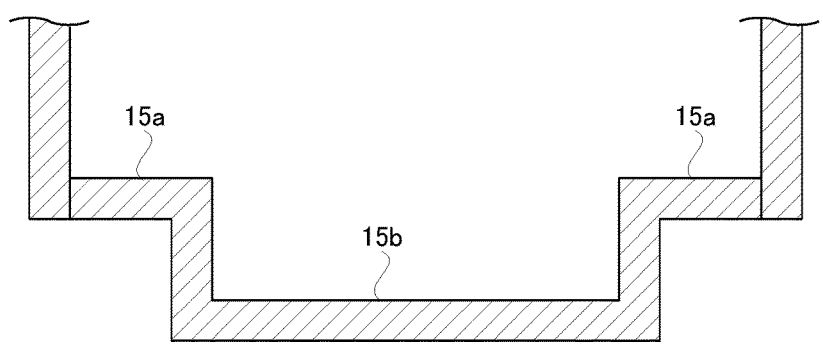

Fig.10
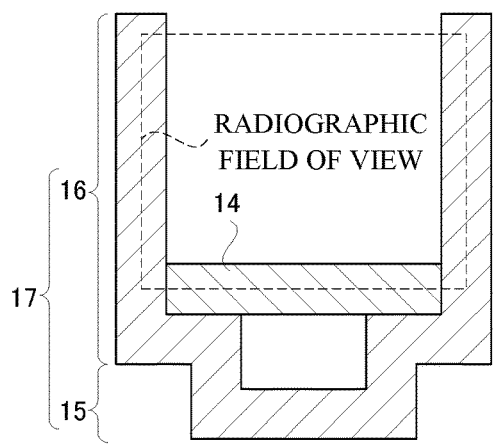
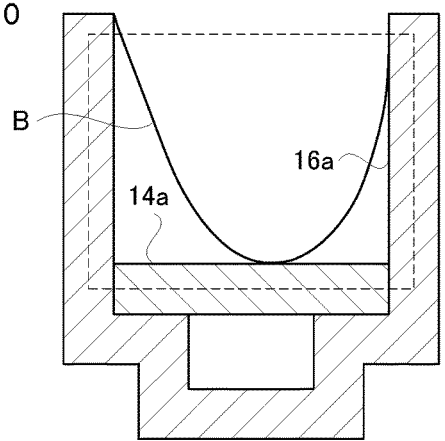
Fig.11
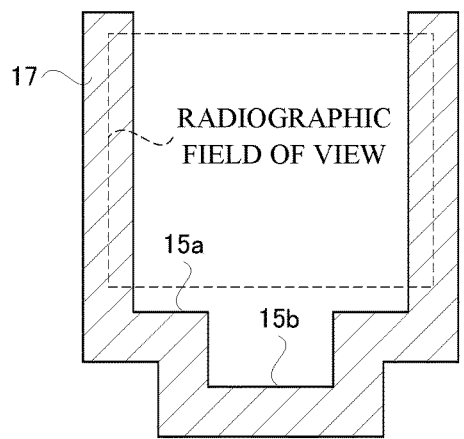
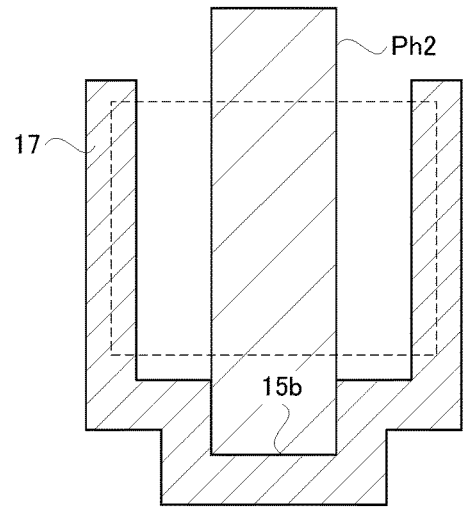
Fig.12
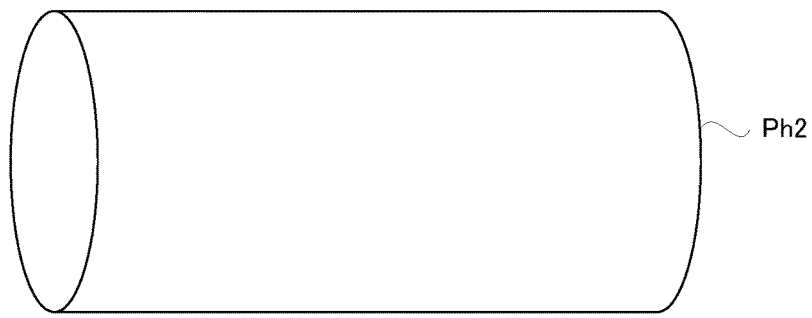

Prior Art

IMAGE PICKUP APPARATUS FOR BREAST EXAMINATION

RELATED APPLICATIONS

This application is the U.S. National Phase under 35 U.S.C. § 371, of International Application No. PCT/JP2014/082890, filed on Dec. 11, 2014 (which claims the benefit of Japanese Application No. 2014-063593, filed on Mar. 26, 2014), the disclosures of which Applications are each incorporated by reference herein.

TECHNICAL FIELD

This invention relates to an image pickup apparatus for breast examination, which detects pairs of annihilation radiation emitted from a patient to image a distribution of a radioactive drug in the patient, and more particularly to an image pickup apparatus for breast examination for use in cancer screening.

BACKGROUND ART

A medical institution has a sectional radiographic apparatus installed therein for imaging a distribution of a radioactive drug. A specific construction of such a sectional radiographic apparatus will be described. A conventional sectional radiographic apparatus has a detector ring with radiation detectors arranged in an annular shape for detecting radiation. This detector ring detects a pair of radiation (pair of annihilation radiation) emitted in opposite directions from a radioactive drug in a patient (see Patent Document 1 and Patent Document 2, for example).

As a type of such sectional radiographic apparatus, there is a sectional radiographic apparatus for breast examination. This image pickup apparatus for breast examination will be described specifically. FIG. 14 is a view illustrating a conventional image pickup apparatus for breast inspection. With a conventional image pickup apparatus 51 for breast inspection, one of the breasts B of a patient M is introduced into a detector ring 62 at the time of examination. In this state, the detector ring 62 detects pairs of annihilation radiation emitted from the patient M.

The detector ring 62 determines a source of the pairs of annihilation radiation emitted from the breast B, and a distribution of the radioactive drug is generated based on this position information. Since the radioactive drug has a property to accumulate more in cancer tissue than normal tissue, breast cancer can be checked by diagnosing a distribution map of the radioactive drug.

PRIOR ART DOCUMENTS

Patent Documents

[Patent Document 1] Unexamined Patent Publication No. 2012-10772
[Patent Document 2] Unexamined Patent Publication No. 2008-99930

SUMMARY OF INVENTION

Technical Problem

However, the image pickup apparatus for breast examination of conventional construction has the following problem.

That is, according to the conventional apparatus, the breasts of patients may protrude from the image pickup apparatus for breast examination.

The sizes of patients' breasts are varied. With the apparatus of conventional construction, when a patient's breast is large, the tip of the breast may project from the detector ring 62. Then, the radioactive drug cannot be imaged for this projecting part of the breast. With the conventional apparatus, therefore, it may be impossible to discover cancer tissue existing at the tip of the breast.

Thus, the entire breast cannot be radiographed reliably unless the breast introduced in the detector ring is securely located in the radiographic field of view of the apparatus.

This invention has been made having regard to the state of the art noted above, and its object is to provide an image pickup apparatus for breast examination which can radiograph entire breasts reliably.

Solution to Problem

To fulfill the above object, this invention provides the following construction.

An image pickup apparatus for breast examination according to this invention comprises (A) a detector ring having a through-hole formed of radiation detectors arranged arcuately for detecting radiation, to provide a radiographic field of view for imaging a drug distribution in a patient; and a support disposed at an opening opposite to an opening at a side, where a breast of the patient is inserted, of the through-hole of the detector ring, and having a contact surface contactable by a tip of the breast of the patient; wherein the contact surface of the support is located in the radiographic field of view.

[Functions and effects] According to this invention, the breast introduced into the detector ring can be positioned reliably in the radiographic field of view of the apparatus. That is, the sectional radiographic apparatus according to this invention has the support at the opening, of the through-hole formed in the detector ring, at the side opposite to the opening at the side for inserting the breast of the patient. The tip of the breast introduced into the detector ring is obstructed by this support, so that it cannot project out of the detector ring but contacts the contact surface of the support located in the radiographic field of view. According to this invention, the tip of the breast does not project out of the radiographic field of view, and the breast introduced into the detector ring can be positioned reliably in the radiographic field of view of the apparatus.

Preferably, the above image pickup apparatus for breast examination comprises (B) a closure member for supporting the support, disposed outside the radiographic field of view, and for closing the opening of the detector ring; wherein the support is attachable to and detachable from the closure member.

[Functions and effects] The above construction is what the apparatus of this invention is made more specific. The support, if attachable to and detachable from the closure member, provides an advantage when carrying out maintenance using a phantom. Such phantom needs to project a tip thereof out of the radiographic field of view in use, and the support will be an obstacle then. If the support is removed, the phantom introduced into the detector ring will be located outside the radiographic field of view, and will contact the closure member closing the opening of the detector ring. According to above construction, therefore, the image pickup apparatus for breast examination can be provided which can perform maintenance with increased facility.

In the above image pickup apparatus for breast examination, it is preferred that (C) the closure member has a recess formed therein for receiving and contacting a tip of a phantom inserted into the detector ring from the opening at the side where the breast is inserted.

[Functions and effects] The above construction is what the apparatus of this invention is made more specific. With the closure member having the recess for receiving and contacting the tip of the phantom inserted into the detector ring from the opening at the side for inserting the breast, it is possible to position the phantom contacted by the closure member. When introducing the phantom into the detector ring, it is necessary to place the phantom in a predetermined position. Otherwise, when an attempt is made to detect radiation emitted from the phantom with the detector ring, detection results will vary with the position of the phantom. Considering that what should be measured using the phantom is, rather, variations with time of the detector ring, it is necessary to always place the phantom introduced into the detector ring in a regular position. According to the above construction, since the closure member plays a role of a jig for positioning the phantom, positioning of the phantom can be performed easily.

Preferably, the above image pickup apparatus for breast examination comprises a cylindrical member of cylindrical shape for covering an inner wall of the detector ring, and having a contact surface contactable by side portions of the breast of the patient; wherein the contact surface of the cylindrical member is located in the radiographic field of view.

[Functions and effects] The above construction is what the apparatus of this invention is made more specific. If the contact surface, contacted by the side portions of the breast, of the cylindrical member of cylindrical shape which covers the inner wall of the detector ring is located within the radiographic field of view, the side portions of the breast introduced into the detector ring are obstructed by this cylindrical member to be unable to approach the detector ring and contact the contact surface located within the radiographic field of view. According to this invention, the side portions of the breast do not bulge out around the inner wall of the detector ring which is outside the radiographic field of view, and the breast introduced into the detector ring can be positioned reliably in the radiographic field of view of the apparatus.

In the above image pickup apparatus for breast examination, it is preferred that the opening at the side, where the breast of the patient is inserted, of the through-hole of the detector ring is positioned vertically upward with respect to the support.

[Functions and effects] The above construction is what the apparatus of this invention is made more specific. If, of the through-hole formed in the detector ring, the opening at the side for inserting the breast of the patient is positioned vertically upward relative to the support, the breast will be introduced from the upper part of the detector ring. Since the breast inside the detector ring tends to hang down under its own weight, the breast is introduced deep into the detector ring reliably. According to this invention, even in such a situation, the presence of the support prevents the tip of the breast from projecting under the detector ring, and the entire breast remains in the radiographic field of view.

This specification also discloses a construction without the support described above.

That is, an image pickup apparatus for breast examination according to this invention may comprise (A) a detector ring having a through-hole formed of radiation detectors arranged arcuately for detecting radiation, to provide a radiographic field of view for imaging a drug distribution in a patient; and (B) a closure member disposed at an opening opposite to an opening at a side, where a breast of the patient is inserted, of the through-hole of the detector ring, and closing the opening of the detector ring; wherein (C) the closure member has a recess formed therein for receiving and contacting a tip of a phantom inserted into the detector ring from the opening at the side where the breast is inserted.

[Functions and effects] According to the above construction, with the closure member having the recess for receiving and contacting the tip of the phantom inserted into the detector ring from the opening at the side for inserting the breast, it is possible to position the phantom contacted by the closure member. When introducing the phantom into the detector ring, it is necessary to place the phantom in a predetermined position. Otherwise, when an attempt is made to detect radiation emitted from the phantom with the detector ring, detection results will vary with the position of the phantom. Considering that what should be measured using the phantom is, rather, variations with time of the detector ring, it is necessary to always place the phantom introduced into the detector ring in a regular position. According to the above construction, since the closure member plays a role of a jig for positioning the phantom, positioning of the phantom can be performed easily.

Advantageous Effects of Invention

According to this invention, a breast introduced into a detector ring can be positioned reliably in a radiographic field of view of the apparatus. That is, the sectional radiographic apparatus according to this invention includes a support disposed at an opening, of a through-hole formed in the detector ring, at a side opposite to an opening at a side for inserting the breast of a patient. The support has a contact surface contactable by the breast and located in the radiographic field of view. The tip of the breast introduced into the detector ring is obstructed by this support, so that it cannot project out of the detector ring but contacts the contact surface located in the radiographic field of view. According to this invention, the tip of the breast does not project out of the radiographic field of view, and the breast introduced into the detector ring can be positioned reliably in the radiographic field of view of the apparatus.

BRIEF DESCRIPTION OF DRAWINGS

FIG. 5 is an exploded perspective view illustrating a cover according to Embodiment 1;

FIG. 6 is a sectional view illustrating a positional relationship between the cover and the support according to Embodiment 1;

FIG. 10 is a schematic view illustrating how a breast is introduced into the cover according to Embodiment 1;

FIG. 11 is a schematic view illustrating how a phantom is introduced into the cover according to Embodiment 1;

FIG. 12 is a perspective view illustrating the phantom according to Embodiment 1.

DESCRIPTION OF EMBODIMENTS

The best mode for carrying out this invention will be described hereinafter with reference to embodiments.

Embodiment 1

An embodiment of a sectional radiographic apparatus according to this invention will be described hereinafter with reference to the drawings. Gamma rays in Embodiment 1 are an example of the radiation in this invention. The construction in Embodiment 1 is a diagnostic imaging apparatus for breast examination. That is, the sectional radiographic apparatus in Embodiment 1 is a type of PET (Positron Emission Tomography) apparatus which images a radioactive drug distributed in breasts B and generates tomographic images. And the apparatus in Embodiment 1 has a construction for radiographing the right breast and left breast of a patient M, i.e. in two separate steps each for one side.

Figure 1:
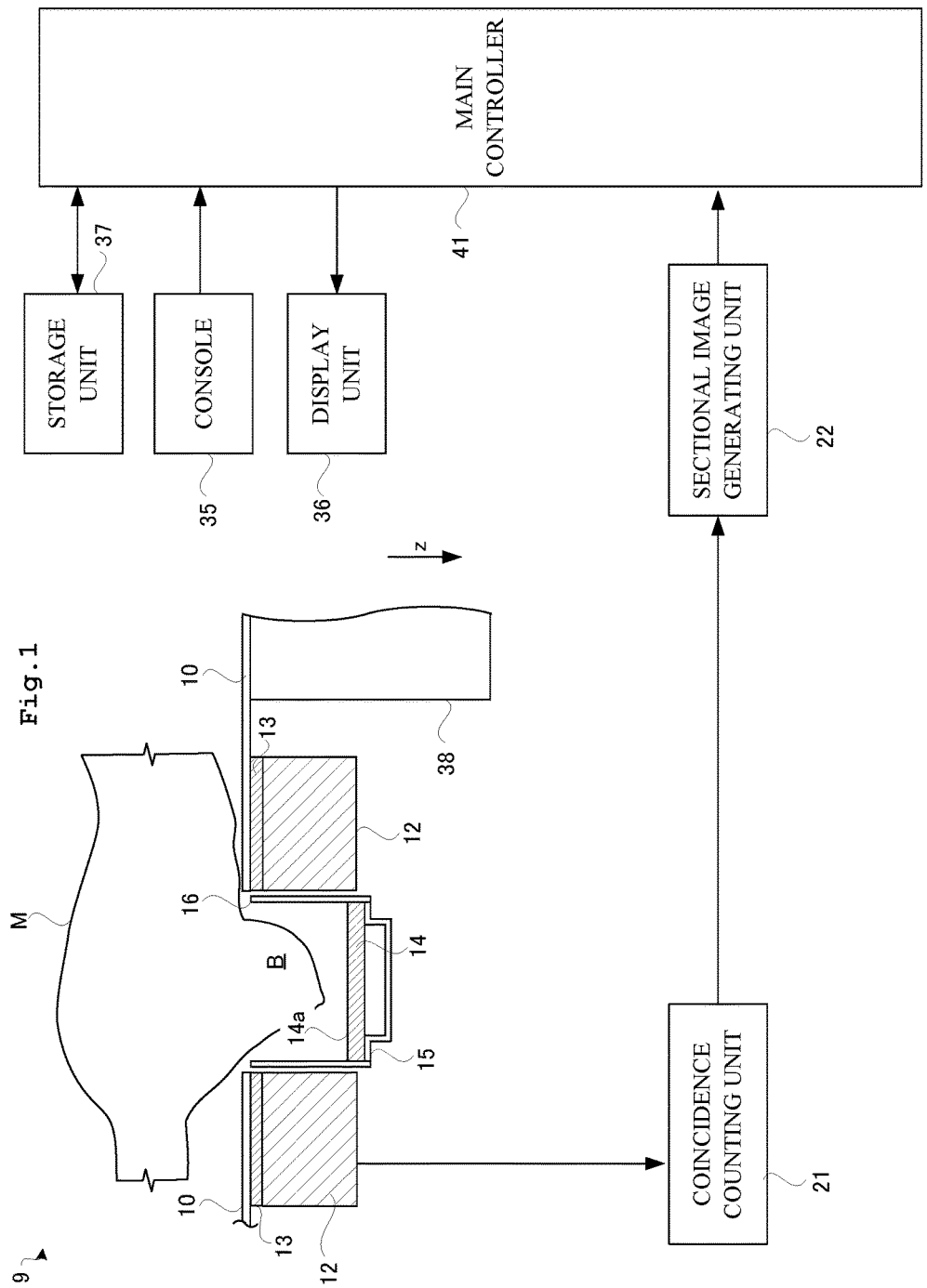
FIG. 1 is a functional block diagram illustrating an overall construction of an image pickup apparatus for breast examination according to Embodiment 1.

FIG. 1 is a functional block diagram illustrating a specific construction of a sectional radiographic apparatus according to Embodiment 1. A sectional radiographic apparatus 9 according to Embodiment 1 includes a cover 17 in a cylindrical shape with an opening for introducing a breast B of the patient M in a z-direction and a closed bottom, and a detector ring 12 in an annular shape mounted to surround a cylindrical portion of the cover 17. An opening portion formed in the detector ring 12 has a cylindrical shape (regular polygonal column, to be exact) extending in the z-direction. Therefore, the detector ring 12 itself also extends in the z-direction. A through-hole formed by radiation detectors 1 arranged arcuately in the detector ring 12 for detecting radiation provides a radiographic field of view when imaging a drug distribution in the patient M. The z-direction extends along a central axis of the detector ring 12. The detector ring 12 is formed of the radiation detectors described hereinafter which are arranged arcuately for detecting radiation. A top board 10, the detector ring 12, a shielding plate 13 and the cover 17 are supported by a support block 38.

The top board 10 is provided for the purpose of supporting the patient M lying on her stomach. The top board 10 has a hole formed to penetrate it in the z-direction for inserting the breast B of the patient M. The breast B is introduced into the cover 17 through this hole. The opening of the cover 17 is formed to face vertically upward, and the breast B will be introduced from a vertically downward direction into this opening. An opening, at a side of insertion of the breast B of the patient M, of the through-hole of the detector ring 12 is located in a vertically upward facing position relative to a support 14 described hereinafter.

The shielding plate 13 is formed of tungsten or lead, for example (see FIG. 1). Since the radioactive drug is present also in parts other than the breast B of the patient M, annihilation gamma ray pairs generate also from such parts. The annihilation gamma ray pairs generating from such parts other than the site of interest and incident on the detector ring 12 will become obstructive to sectional image radiography. So the ring-shaped shielding plate 13, which absorbs gamma rays, is provided to cover one end of the detector ring 12 close to the patient M in the z-direction. The shielding plate 13 is located in a position clamped between the top plate 10 and the detector ring 12.

Figure 2:
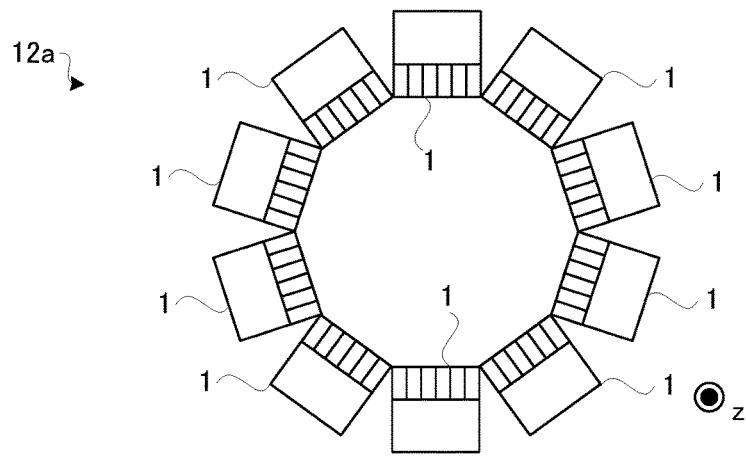
FIG. 2 is a plan view illustrating a detector ring according to Embodiment 1.

The construction of the detector ring 12 will be described. The detector ring 12 has one unit ring 12a formed, for example, of ten radiation detectors 1 arranged in a virtual circle on a plane perpendicular to the z-direction (the direction of the central axis). The detector ring 12 is constructed of three of this unit ring 12a arranged in the z-direction, for example (see FIG. 2 for specifics).

Figure 3:
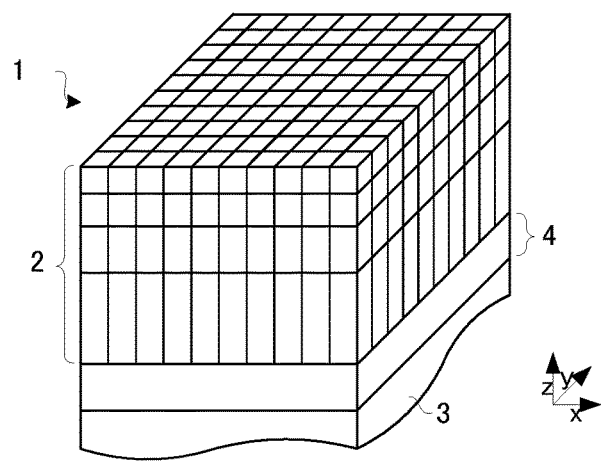
FIG. 3 is a perspective view illustrating a radiation detector according to Embodiment 1.

The construction of radiation detectors 1 will be described briefly. FIG. 3 is a perspective view illustrating the construction of a radiation detector according to Embodiment 1. As shown in FIG. 3, the radiation detector 1 includes a scintillator 2 for converting radiation into light, and a photodetector 3 formed of a photomultiplier for detecting the light. A light guide 4 is interposed between the scintillator 2 and photodetector 3 for receiving and delivering the light.

The scintillator 2 is constructed of scintillator crystals arranged in three dimensions. The scintillator crystals are formed of $Lu_{2(1-X)}Y_{2X}SiO_5$ (hereinafter referred to as LYSO) with Ce diffused. The photodetector 3 can determine positions of occurrence of light, i.e. which scintillator crystals emit light, and can determine also intensity of the light and time at which the light occurs. The construction of the scintillator 2 in Embodiment 1 is only an example that can be employed. Therefore, the construction of this invention is not limited to this.

A coincidence counting unit 21 (see FIG. 1) receives detection signals outputted from the detector ring 12. Two gamma rays incident on the detector ring 12 at the same time are an annihilation gamma ray pair due to the radioactive drug in the patient. The coincidence counting unit 21 counts the number of times annihilation gamma ray pairs are detected by every combination of two of the scintillator crystals forming the detector ring 12, and outputs the results to a sectional image generating unit 22. Time information applied to the detection signals by a clock is used by the coincidence counting unit 21 in determining coincidences of the detection signals. The detection signals outputted to the coincidence counting unit 21 show detection results of radiation derived from the radioactive drug administered to the patient M.

The coincidence counting unit 21 outputs data concerning results of coincidence counting to the sectional image generating unit 22. Based on this data, the sectional image generating unit 22 generates sectional images by imaging a distribution of the radioactive drug in the radiographic field of view located inside the detector ring 12.

Figure 4:
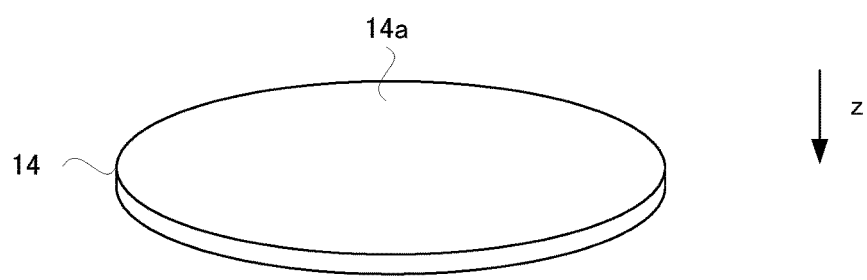
FIG. 4 is a perspective view illustrating a support according to Embodiment 1.

FIG. 4 illustrates a construction of the support 14 according to this invention. The support 14 is a disk-shaped member provided for the opening of the cover 17, and a member laid in a bottom plane of the cover 17 and having a direction of thickness thereof coinciding with the z-direction. This support 14 is also a member contactable by the tip of the breast B of the patient M introduced into the cover 17. Of the surfaces of the support 14, the one contacted by the breast B will be called a contact surface 14a. Thus, the support 14 is located in the opening of the through-hole of the detector ring 12, which is opposite to the opening at the side where the breast B of the patient M is inserted, and has the contact surface 14a contactable by the tip of the breast B of the patient M. The support 14 is attachable to and detachable from a closure member 15 described hereinafter. However, the breast B of the patient M has varied sizes and forms. Therefore, when the breast B is small, the breast B may not contact the support 14.

FIG. 5 is an exploded perspective view illustrating a construction of the cover 17 according to this invention. The cover 17 is a member for protecting the breast B, which is provided so that the breast B of the patient M will not directly contact the detector ring 12, and is also a member disposed in the opening of the detector ring 12. The cover 17 includes a cylindrical member 16 having a cylindrical shape which follows the shape of the opening of the detector ring 12. The cylindrical member 16 is a cylinder-shaped member covering an inner wall of the detector ring 12, and having a contact surface 16a contactable by side portions of the breast B of the patient M. The cylindrical member 16 has an outside diameter slightly shorter than the inner wall of the detector ring 12. Therefore, only a small gap is formed between the cylindrical member 16 and the detector ring 12. The cylindrical member 16 has an inner wall thereof acting as the contact surface 16a contactable by the breast B of the patient M. The breast B of the patient M has varied sizes and forms. Therefore, when the breast B is small, the breast B may not contact the contact surface 16a.

The cover 17 is fixed to the apparatus to have a central axis of the cylindrical member 16 coinciding with the central axis of the inner wall of the detector ring 12.

The cover 17 includes a closure member 15 for closing one end of the cylinder member 16 as shown in FIG. 5. The closure member 15 is a member which closes the bottom of the cylindrical member 16 extending in the z-direction (vertical direction), and is disk-shaped with a circular recess formed centrally thereof. This recess extends in a direction (z-direction) away from the cylinder member 16, has a central axis thereof coinciding with the central axis of the inner wall of the detector ring 12, and has a cylindrical shape with a closed bottom. An annular portion with a central axis located around the recess of the closure member 15 acts as a contact surface 15a contactable by the support 14. The bottom surface of the recess of the closure member 15 provides a contact surface 15b contactable by a tip of a phantom Ph2 described hereinafter.

The support 14 can be attached to and detached from the closure member 15 of the cover 17, and this construction will be described. The upper part of FIG. 6 depicts a state in which the support 14 is laid on the bottom of the cover 17. The support 14 at this time covers the entire plane of the closure member 15 of the cover 17. When one looks down at the bottom from the opening of the cover 17, the closure member 15 is invisible.

The lower part of FIG. 6 depicts a state in which the support 14 is removed from the cover 17. When one looks down at the bottom from the opening of the cover 17, the closure member 15 and the recess are visible.

<About Radiographic Field of View>

The radiographic field of view of the detector ring 12 will now be described. The radiographic field of view is a range which enables imaging of a distribution of the radioactive drug, and the apparatus cannot image the radioactive drug in a position outside this radiographic field of view. The radiographic field of view is determined by a position of the detector ring 12. The radiographic field of view is a space in a cylindrical shape surrounded by the detector ring 12.

Figure 7:
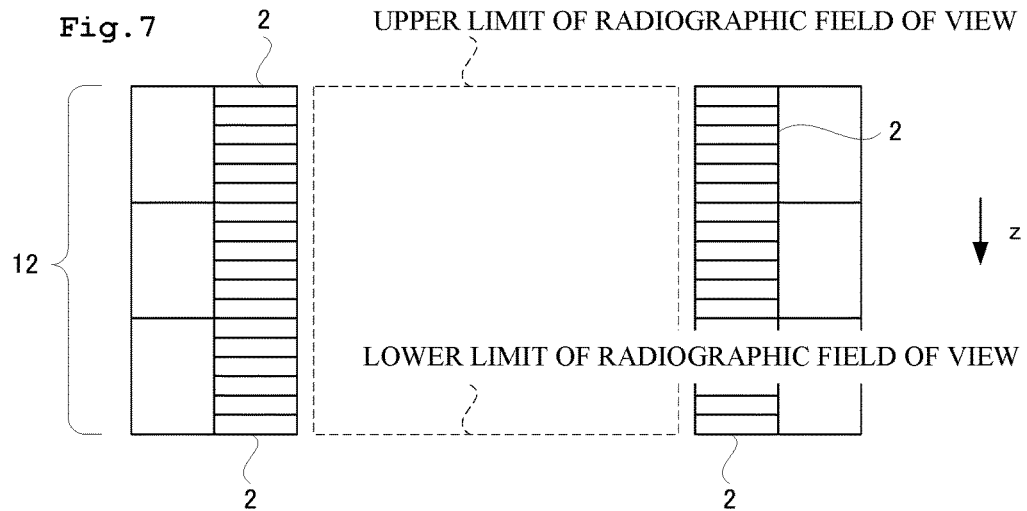
FIG. 7 is a sectional view illustrating a radiographic field of view according to Embodiment 1.

This radiographic field of view does not vaguely mean a space inside the detector ring 12, but its range is more strictly determined. What determines dimensions with respect to the z-direction of the radiographic field of view is positions of the scintillators 2 provided for the detector ring 12. That is, as shown in FIG. 7, the height of an upper limit of the radiographic field of view corresponds to the height of upper surfaces of the scintillators 2 of the radiation detectors 1 located in an uppermost position among the radiation detectors 1 constituting the detector ring 12. The height of a lower limit of the radiographic field of view, as shown in FIG. 7, corresponds to the height of lower surfaces of the scintillators 2 of the radiation detectors 1 located in a lowermost position among the radiation detectors 1 constituting the detector ring 12. In this way, a length of the cylindrical radiographic field of view is determined by the positions of the scintillators 2.

In some cases, the radiographic field of view is required to be narrower than this due to a necessity for clearer imaging of the radioactive drug. Even in such cases, the upper limit of the radiographic field of view is not set to a position higher than the height of the upper surfaces of the scintillators 2 of the radiation detectors 1 located in the uppermost position among the radiation detectors 1 constituting the detector ring 12. Nor is the lower limit of the radiographic field of view set to a position lower than the height of the lower surfaces of the scintillators 2 of the radiation detectors 1 located in the lowermost position among the radiation detectors 1 constituting the detector ring 12.

Then, how is a diameter of the cylindrical radiographic field of view determined? At least the diameter of the radiographic field of view cannot be set larger than the diameter of the inner wall of the detector ring 12. It is because the radiographic field of view cannot be set to the interiors of the scintillators 2 taking part in detection of the radiation. That is to say, if the diameter of the radiographic field of view were made to correspond to the diameter of the inner wall of the detector ring 12, the radiographic field of view would conveniently become the largest. It seems possible to make the diameter of the radiographic field of view correspond to the inside diameter of the detector ring 12.

However, the diameter of the actual radiographic field of view will become smaller than the inside diameter of the detector ring 12. This situation will be explained. The radiation detectors 1 constituting the detector ring 12 do not all detect the radiation uniformly. The radiation detectors 1 have variations in detection sensitivity which can also be called individual differences. When the radioactive drug is imaged disregarding these variations, the variations in detection sensitivity will be superimposed on the distribution image of the radioactive drug. So, the construction of this invention is based on a prior knowledge of the way the variations in detection sensitivity are distributed over the detector ring 12. It is because the variations in detection sensitivity can be eliminated from the distribution image of the radioactive drug if these sensitivity variations are known in advance. Such sensitivity variations can be obtained by actual measurement using the radioactive drug.

Figure 8:
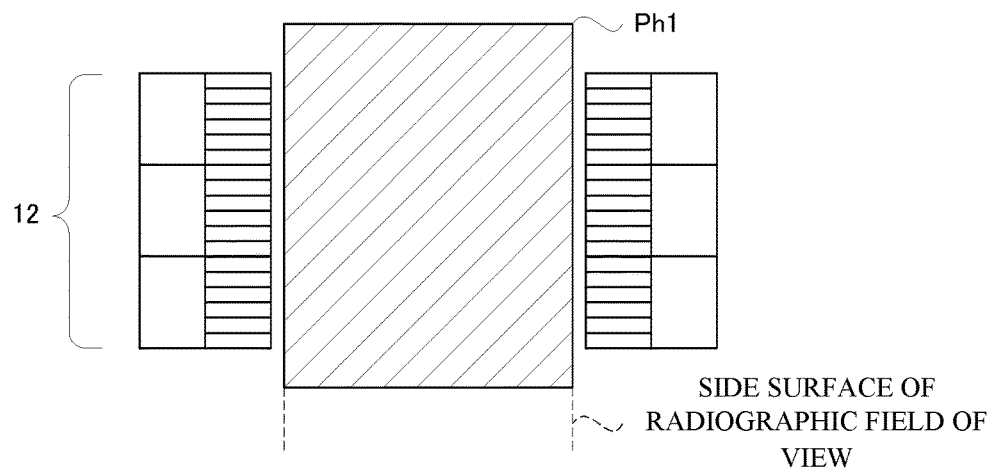
FIG. 8 is a sectional view illustrating the radiographic field of view according to Embodiment 1.

FIG. 8 shows how the sensitivity variations are actually measured. Since this actual measurement of the sensitivity variations is carried out before the detector ring 12 is incorporated into the apparatus, the cover 17 is not yet placed inside the detector ring 12. It is therefore not necessary to consider interference between phantom Ph1 and cover 17. As shown in FIG. 8, the detector ring 12 has inserted therein a ring-shaped phantom Ph1 extending in the z-direction. This phantom Ph1 is longer than the thickness in the z-direction of the detector ring 12. When setting the phantom Ph1 to the detector ring 12, the phantom Ph1 is placed to project from the opposite, upper and lower sides of the detector ring 12. In this way, the phantom Ph1 can be introduced reliably into the detector ring 12 to enable collection of detection data with increased reliability.

To introduce the phantom Ph1 into detector ring 12, a clearance is required between the inner wall of detector ring 12 and the phantom Ph1. The phantom Ph1 is a tank filled with water in which the radioactive drug has solved. A housing for forming this tank is plastic, for example, and radiation is not emitted therefrom. Therefore, even if the phantom Ph1 is inserted in the detector ring 12, the radioactive drug cannot be positioned throughout the interior of the detector ring 12.

In fact, an area of distribution of the radioactive drug in the state of the phantom Ph1 being inserted determines the radiographic field of view. What is known from the introduction of the phantom Ph1 into the detector ring 12 is, to be exact, how artifacts resulting from the variations in detection sensitivity of the radiation detectors 1 are distributed in the interior space of the detector ring 12. The variations in detection sensitivity are made into data as a three-dimensional sensitivity map of the detectors.

When the breast B of the patient M is introduced into the detector ring 12 and the radioactive drug is imaged, an image obtained has virtual images due to the sensitivity variations superimposed on a distribution image of the radioactive drug. These virtual images are erased by uniforming the sensitivity variations of the detectors based on the sensitivity map obtained from the actual measurement. Therefore, a spatial range for removing the virtual images from the image obtained by introducing the breast B of the patient M is limited to the range of this sensitivity map. In other words, if not within the range of the sensitivity map, a clear imaging of the radioactive drug distribution cannot be performed. It is spatial limits of this sensitivity map that determine limits of the radiographic field of view. In other words, the phantom Ph1 determines a side surface of the radiographic field of view (see FIG. 8). To be more accurate, the side surface of the radiographic field of view coincides with the inner surface contacted by the water containing the radioactive drug in the housing forming the phantom Ph1.

The radiographic field of view may be made narrower than this from a necessity to image the radioactive drug more clearly. Even in such a case, the side surface of the radiographic field of view is set closer to the central axis of the detector ring 12 than the inner surface contacted by the water containing the radioactive drug in the housing forming the phantom Ph1. Consequently, the radiographic field of view has a diameter smaller than the radiographable cylindrical range determined by the phantom.

Figure 9:
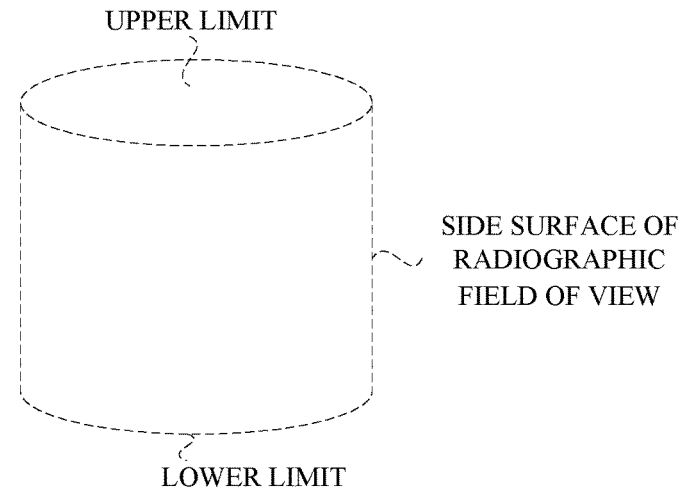
FIG. 9 is a sectional view illustrating the radiographic field of view according to Embodiment 1.

The above situation is summarized as follows. FIG. 9 depicts a cylindrical radiographic field of view. Its upper limit and lower limit are determined by the positions of the scintillators 2 included in the detector ring 12. The side surface is determined by the shape of the phantom Ph1 for calibration.

<Positional Relationship Between Radiographic Field of View and Each Member>

Next, a positional relationship between the radiographic field of view and each member, which is the most salient characteristic of this invention, will be described. The left side of FIG. 10 shows what positional relationship the cover 17 and the support 14 mounted on the bottom of the cover 17 have with respect to the radiographic field of view. The support 14 in contact with the contact surface 15a of the closure member 15 on the bottom of the cover 17 has a position and size which embrace a circular plane indicating the lower limit of the radiographic field of view. Therefore, the contact surface 14a of the support 14 is located above the lower limit of the radiographic field of view, and as a result located inside the radiographic field of view. The surface of the support 14 that contacts the closure member 15 is located below the lower limit of the radiographic field of view, and as a result located outside the radiographic field of view. That is, the circular plane indicating the lower limit of the radiographic field of view is located in a middle position between the above two surfaces, and is located inside the support 14. Of the support 14, a portion near the opening of the cover 17 belongs to the radiographic field of view, and a portion near the closure member 15 (portion far from the opening of the cover 17) lies outside the radiographic field of view. Incidentally, the closure member 15 which supports the support 14 is disposed outside the radiographic field of view.

With such construction, when the breast B of the patient M is introduced from the opening of the cover 17, the breast B will not protrude outside the radiographic field of view. The breast B introduced from the opening of the cover 17, as shown on the right side in FIG. 10, has its tip in contact with the contact surface 14a of the support 14. The breast B at this time is obstructed by the support 14 and cannot project outside beyond this. It is because the contact surface 14a is located in a position belonging to the radiographic field of view including the lower end of the field.

On the other hand, the cylindrical member 16 which is a constituent member of the cover 17 has a top height thereof higher than an upper plane of the radiographic field of view. It is because of a necessity to form no gap through which side portions of the breast B might bulge out toward the detector ring 12. When the breast B of the patient M is set to the apparatus, the entire breast B cannot be introduced into the radiographic field of view. The base portion of the breast B will be located outside the radiographic field of view. This portion, although located outside the radiographic field of view, should not protrude toward the detector ring 12. This is because of a necessity to introduce the breast B reliably into the radiographic field of view and a necessity to ensure safety.

Next, the diameters of the cylindrical member 16 will be described. The cylindrical member 16 of the cover 17 has such an outside diameter and an inside diameter that can embrace a cylindrical plane indicating a range for the side surface of the radiographic field of view. That is, a cylindrical curved surface (contact surface 16a) that determines the inside diameter of the cylindrical member 16 is within the range of the radiographic field of view, and a cylindrical curved surface that determines the outside diameter of the cylindrical member 16 is outside the radiographic field of view range. Consequently, the cylindrical plane indicating the range for the side surface of the radiographic field of view is located in a middle position between the above two curved surfaces, and is located in the interior of the cylindrical member 16. Of the cylindrical member 16, a portion near the central axis belongs to the radiographic field of view, and a portion near the detector ring 12 (portion far from the central axis) is outside the radiographic field of view.

With such construction, when the breast B of the patient M is introduced from the opening of the cover 17, the breast B will not protrude outside the radiographic field of view.

The breast B introduced from the opening of the cover 17, as shown on the right side in FIG. 10, has its side surface in contact with the contact surface 16a of the cylindrical member 16. The breast B at this time is obstructed by the cylindrical member 16 and cannot bulge outside beyond this. It is because the contact surface 16a is located in a position belonging to the radiographic field of view.

As described above, the breast B introduced from the opening of the cover 17, with its tip obstructed by the support member 14 and the side obstructed by the cylindrical member 16, respectively, cannot project or bulge out toward the radiographic field of view. According to this invention, the whole region of the breast can fit in the radiographic field of view as much as possible.

<Removal of Support>

The above support 14 is removable from the bottom of the cover 17. The meaning of this construction will be described. The left side in FIG. 11 shows a state in which the support 14 has been removed from the cover 17. If the breast B were inserted from the opening of the cover 17 in this state, the tip of the breast B could protrude from the radiographic field of view. Therefore, insertion of the breast B is not carried out in the state of the support 14 having been removed. It is a phantom for maintenance Ph2 as shown on the right side in FIG. 11 that is inserted in the cover 17 when there is no support 14. This phantom Ph2 has a cylindrical shape with a length longer than the radiographic field of view as does the phantom Ph1, but has a smaller diameter than the phantom Ph1. The phantom Ph2 can therefore be introduced into the detector ring 12 even when the cover 17 is in place.

FIG. 12 depicts an outer configuration of the phantom Ph2. This phantom Ph2 is used when measuring variations with time of the radiation detectors 1 constituting the detector ring 12, and is a component necessary for maintenance of the apparatus. As is the phantom Ph1, the phantom Ph2 is a tank containing water with the radioactive drug dispersed therein. Variations with time of the radiation detectors 1 can be grasped by causing the radiation detectors 1 to detect radiation emitted from the phantom Ph2.

The shape at the tip of the phantom Ph2 and the recess formed in the closure member 15 are in complementary shape, and the tip of the phantom Ph2 can be fitted in the recess. That is, the recess of the closure member 15 is formed for the purpose of receiving and contacting the tip of the phantom Ph2 inserted in the detector ring 12 from the opening at the side for inserting the breast B. At this time, the tip of the phantom Ph2 can contact the contact surface 15b formed in the bottom of the recess.

Thus, the closure member 15 also serves as a jig for positioning the phantom Ph2. The phantom Ph2 is positioned by the closure member 15 to have a central axis thereof in the same position as the central axis of the detector ring 12. By unambiguously determining the position of the radiation source in this way, detection data can be collected with increased reliability. When the positional relationship between the phantom Ph2 and detector ring 12 does not become a predetermined one, detection results will vary with a relative position between the phantom Ph2 and detector ring 12, making it impossible to measure variations with time of the radiation detectors 1 accurately. According to this invention, such a situation will not arise.

<Positional Relationship of Between Radiographic Field of View and Closure Member>

Next, a positional relationship between a lower part of the radiographic field of view and the closure member 15 will be described. The contact surface 15a for the support 14 and the contact surface 15b for the phantom Ph2, which are provided for the closure member 15, are located below the circular plane indicating the lower limit of the radiographic field of view, and both are outside the radiographic field of view. Therefore, when the tip of the phantom Ph2 is inserted in the recess of the closure member 15, the tip of the phantom Ph2 will be located on the contact surface 15b outside the radiographic field of view. Thus, as shown on the right side in FIG. 11, when the phantom Ph2 is set to the cover 17, the phantom Ph2 will be in a state of projecting from both the upper and lower sides of the detector ring 12. This allows the phantom Ph2 to be introduced into the detector ring 12 reliably, to enable collection of detection data with increased reliability. In a state where the support 14 exists in the bottom of the cover 17, the recess for receiving the phantom Ph2 is not exposed. Then the phantom Ph2 cannot be positioned, and the phantom Ph2 is unable to project from under the radiographic field of view. In this invention, therefore, the phantom Ph2 is not inserted in the cover 17 in the state where the support 14 exists in the bottom of the cover 17.

The sectional radiographic apparatus 9 includes a main controller 41 for performing overall control of the various components. This main controller 41 is constructed of a CPU for executing various programs to realize the respective components 21 and 22. The above components may be realized by being divided into control devices which take charge thereof. A console 35 is provided for the operator to input various instructions and data. A display unit 36 is provided for displaying sectional images generated by the sectional image generating unit 22. A storage unit 37 stores all of the data required for operation of the apparatus.

According to this invention, as described above, the breast B introduced into the detector ring can be positioned reliably in the radiographic field of view of the apparatus. That is, the sectional radiographic apparatus 9 according to this invention has the support 14 at the opening, of the through-hole formed in the detector ring 12, at the side opposite to the opening at the side for inserting the breast B of the patient M. The tip of the breast B introduced into the detector ring 12 is obstructed by this support 14, so that it cannot project out of the detector ring 12 but contacts the contact surface 14a of the support 14 located in the radiographic field of view. According to this invention, the tip of the breast B does not project out of the radiographic field of view, and the breast B introduced into the detector ring can be positioned reliably in the radiographic field of view of the apparatus.

As described above, the support 14, if attachable to and detachable from the closure member 15, provides an advantage when carrying out maintenance using the phantom Ph2. Such phantom Ph2 needs to project the tip thereof out of the radiographic field of view in use, and the support 14 will be an obstacle then. If the support 14 is removed, the phantom Ph2 introduced into the detector ring will be located outside the radiographic field of view, and will contact the closure member 15 closing the opening of the detector ring 12. According to above construction, therefore, the image pickup apparatus for breast examination can be provided which can perform maintenance with increased facility.

As described above, with the closure member 15 having the recess for receiving and contacting the tip of phantom Ph2 inserted into the detector ring 12 from the opening at the side for inserting the breast B, it is possible to position the phantom Ph2 contacted by the closure member 15. When introducing the phantom Ph2 into the detector ring 12, it is necessary to place the phantom Ph2 in a predetermined position. Otherwise, when an attempt is made to detect radiation emitted from the phantom Ph2 with the detector ring 12, detection results will vary with the position of the phantom Ph2. Considering that what should be measured using the phantom Ph is, rather, variations with time of the detector ring 12, it is necessary to always place the phantom Ph2 introduced into the detector ring 12 in a regular position. According to the above construction, since the closure member 15 plays a role of a jig for positioning the phantom Ph2, positioning of the phantom Ph2 can be performed easily.

If the contact surface 16a, contacted by the side portions of the breast B, of the cylindrical member 16 of cylindrical shape which covers the inner wall of the detector ring 12 is located within the radiographic field of view, the side portions of the breast B introduced into the detector ring 12 are obstructed by this cylindrical member 16 to be unable to approach the detector ring 12 and contact the contact surface 16a located within the radiographic field of view. According to this invention, the side portions of the breast B do not bulge out around the inner wall of the detector ring 12 which is outside the radiographic field of view, and the breast B introduced into the detector ring can be positioned reliably in the radiographic field of view of the apparatus.

And, as described above, if, of the through-hole formed in the detector ring 12, the opening at the side for inserting the breast B of the patient M is positioned vertically upward relative to the support 14, the breast B will be introduced from the upper part of the detector ring 12. Since the breast B inside the detector ring 12 tends to hang down under its own weight, the breast B is introduced deep into the detector ring 12 reliably. According to this invention, even in such a situation, the presence of the support 14 prevents the tip of the breast B from projecting under the detector ring 12, and the entire breast B remains in the radiographic field of view.

Figure 13:
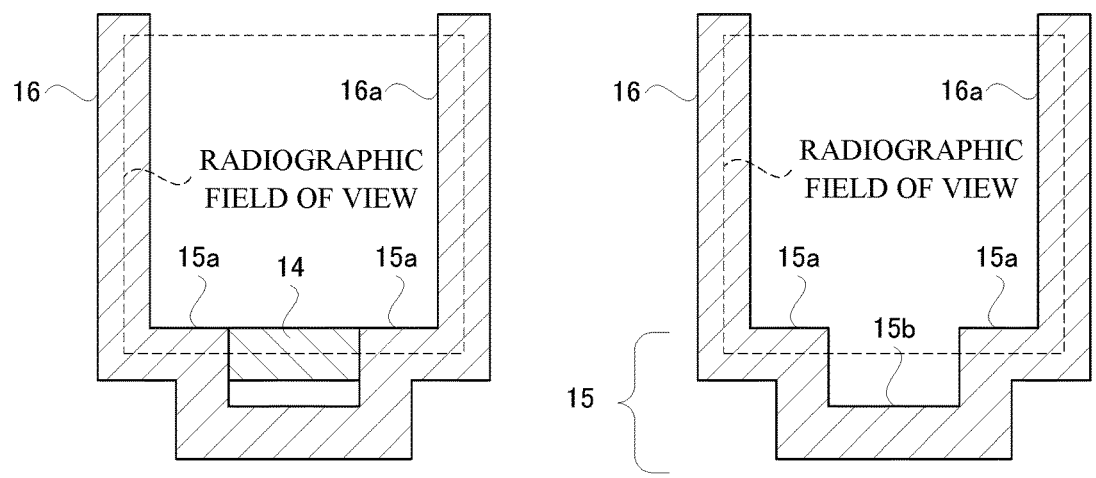
FIG. 13 is a sectional view illustrating one modification of this invention.
Figure 14:
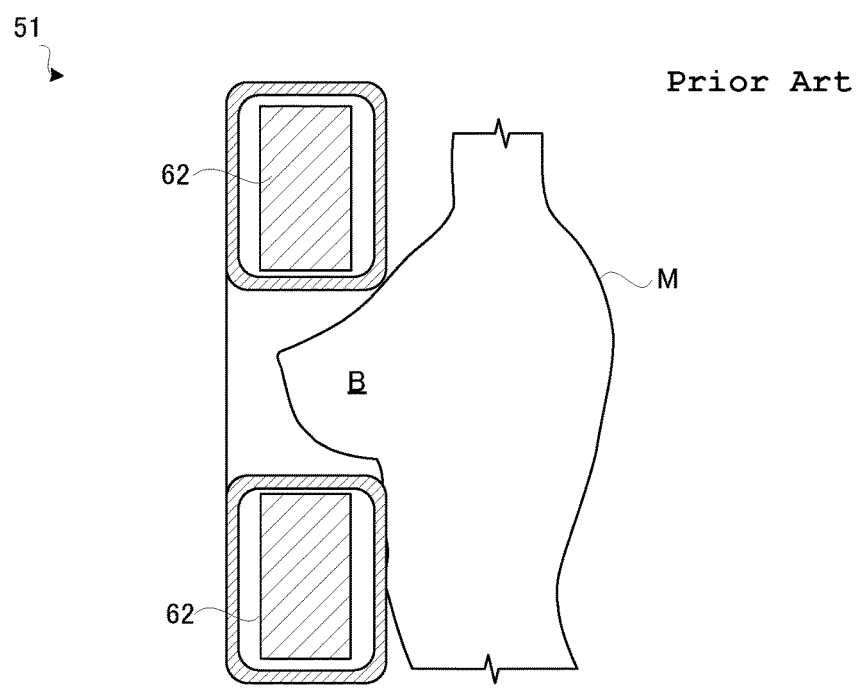
FIG. 14 is a schematic view illustrating an apparatus of conventional construction.

This invention is not limited to the construction described above, but may be modified out as follows:

(1) According to the above construction, the support 14 is made to cover the entire surface of the closure member 15, but this invention is not limited to this construction. As shown on the left side in FIG. 13, the support 14 may be constructed to cover the recess formed in the closure member 15. In this case, the vicinity of the recess of the closure member 15 serves as contact surface 15a contactable by the tip of the breast B of the patient M. As does the contact surface 14a of the support 14 contacted by the tip of the breast B of the patient M, this contact surface 15a belongs to the radiographic field of view including the lower end of the field of view. The contact surface for the phantom Ph2 in the recess of the closure member 15 is outside the radiographic field of view.

(2) Although the surface of the support 14 for contacting the closure member 15 is located outside the radiographic field of view, part or all of this surface may be placed within the range of the radiographic field of view.

(3) According to the construction described hereinbefore, the curved surface in cylindrical shape which determines the outside diameter of the cylindrical member 16 is located outside the radiographic field of view range. However, part or all of this curved surface may be placed within the range of the radiographic field of view.

(4) Although the construction described hereinbefore includes the support 14, this invention is not limited to this construction. That is, this invention may provide a construction without the support 14 as shown on the right side in FIG. 13. According to this modification, the contact surface 15a, contacted by the breast, in the closure member 15 at the bottom of the cover 17 is located closer to the center (upward) of the detector ring 12 than the circular plane indicating the lower limit of the radiographic field of view. With such construction, when the breast B of the patient M is introduced from the opening of the cover 17, the breast B will not protrude outside the radiographic field of view. The breast B introduced from the opening of the cover 17 will have the tip thereof contact the contact surface 15a of the closure member 15. The breast B at this time is obstructed by the contact surface 15a and cannot project outside beyond this. It is because the contact surface 15a is located in the position belonging to the radiographic field of view including the lower end of the field of view.

On the other hand, the contact surface 15b for the phantom Ph2, which is the bottom surface of the recess of the closure member 15, is located below the circular plane indicating the lower limit of the radiographic field of view, and deviates from the radiographic field of view. Therefore, when the tip of the phantom Ph2 is fitted in the recess of the closure member 15, the tip of the phantom Ph2 will be located on the contact surface 15b outside the radiographic field of view. When the phantom Ph2 is set to the cover 17 in this way, the phantom Ph2 will be in a state of projecting from both upper and lower sides of the detector ring 12. In this way, the phantom Ph2 can be introduced reliably into the detector ring 12 to enable collection of detection data with increased reliability.

According to this modification, the breast B introduced from the opening of the cover 17 may partly enter the recess of the closure member 15. When this happens, the tip of the breast B will be located outside the radiographic field of view. Even in such a situation, however, a large part of the tip of the breast B introduced into the cover 17 will contact the contact surface 15a, with only a very slight portion of the breast B located outside the radiographic field of view. Therefore, even if the breast B enters the recess of the closure member 15, it will not pose a particularly big problem.

INDUSTRIAL UTILITY

As described above, this invention is suitable for medical apparatus.

REFERENCE SIGNS LIST 12 detector ring
14 support
15 closure member
16 cylindrical member

The invention claimed is:

1. An image pickup apparatus for breast examination comprising:
   (A) a detector ring having a through-hole formed of radiation detectors arranged arcuately for detecting radiation, to provide a radiographic field of view for imaging a drug distribution in a patient; and
   a support provided, before insertion of a breast into the detector ring, for an opening opposite to an opening at a side, where a breast of the patient is inserted, of the through-hole of the detector ring, and having a contact surface contactable by a tip of the breast of the patient; and
   a cylindrical member of cylindrical shape for covering an inner wall of the detection ring;
   wherein the contact surface of the support is located in the radiographic field of view including a lower end of the field of view, wherein the support is a disk-shaped member having a uniform thickness in a vertically downward direction with respect to the contact surface of the support, the support contacting the cylindrical member.

2. The image pickup apparatus for breast examination according to claim 1, comprising: (B) a closure member for supporting the support, disposed outside the radiographic field of view, and for closing the opening of the detector ring;
wherein the support is attachable to and detachable from the closure member.

3. The image pickup apparatus for breast examination according to claim 2, wherein: (C) the closure member has a recess formed therein for receiving and contacting a tip of a phantom inserted into the detector ring from the opening at the side where the breast is inserted.

4. The image pickup apparatus for breast examination according to claim 1,
wherein the cylindrical member has a contact surface contactable by side portions of the breast of the patient, and
wherein the contact surface of the cylindrical member is located in the radiographic field of view.

5. The image pickup apparatus for breast examination according to claim 1, wherein the opening at the side, where the breast of the patient is inserted, of the through-hole of the detector ring is positioned vertically upward with respect to the support.

6. The image pickup apparatus of claim 1, wherein an upper end of the radiographic field of view and the lower end of the radiographic field of view are respectively determined by the locations of uppermost radiation detectors of the detector ring and the locations of lowermost detectors of the detector ring.

7. An image pickup apparatus for breast examination comprising:
(A) a detector ring having a through-hole formed of radiation detectors arranged arcuately for detecting radiation, to provide a radiographic field of view for imaging a drug distribution in a patient; and
(B1) a closure member provided, before insertion of a breast into the detector ring, for an opening opposite to an opening at a side, where a breast of the patient is inserted, of the through-hole of the detector ring, and closing the opening of the detector ring; and
a cylindrical member of cylindrical shape for covering an inner wall of the detection ring;
wherein (C1) the closure member has a contact surface contactable by a tip of the breast of the patient, and a recess formed therein configured to receive and contact a tip of a phantom inserted into the detector ring from the opening at the side where the breast is inserted, the contact surface being positioned in the radiographic field of view including a lower end of the field of view, and
wherein the closure member is disk-shaped, the closure member contacting the cylindrical member.

8. The image pickup apparatus for breast examination according to claim 7,
wherein the cylindrical member has a contact surface contactable by side portions of the breast of the patient, and
wherein the contact surface of the cylindrical member is located in the radiographic field of view.

9. The image pickup apparatus for breast examination according to claim 7, wherein the opening at the side, where the breast of the patient is inserted, of the through-hole of the detector ring is positioned vertically upward with respect to the support.

10. An image pickup apparatus for breast examination comprising:
(A) a detector ring having a through-hole formed of radiation detectors arranged arcuately for detecting radiation, to provide a radiographic field of view for imaging a drug distribution in a patient; and
a support provided, before insertion of a breast into the detector ring, for an opening opposite to an opening at a side, where a breast of the patient is inserted, of the through-hole of the detector ring, and having a contact surface contactable by a tip of the breast of the patient;
a cylindrical member of cylindrical shape for covering an inner wall of the detection ring; and
a closure member closing the opening of the detector ring, the closure member having a recess formed therein for receiving and contacting a tip of a phantom inserted into the detector ring from the opening at the side where the breast is inserted;
wherein the support is attachable to and detachable from the closure member,
wherein the contact surface of the support is located in the radiographic field of view including a lower end of the field of view,
wherein the support is a disk-shaped member having a uniform thickness in a vertically downward direction with respect to the contact surface of the support.

11. The image pickup apparatus for breast examination according to claim 10, wherein the entire closure member is disposed outside the radiographic field of view.

12. The image pickup apparatus for breast examination according to claim 10, wherein at least a portion of the closure member is disposed inside the radiographic field of view.

* * * * *